(12) United States Patent
LaBorde et al.

(10) Patent No.: US 7,547,557 B2
(45) Date of Patent: Jun. 16, 2009

(54) DIRECTED-FLOW ASSAY DEVICE (75) Inventors: Ronald T. LaBorde, San Diego, CA (US); Herbert S. Chow, San Diego, CA (US)

(73) Assignee: Quantum Design, Inc., San Diego, CA (US)

( * ) Notice: Subject to any disclaimer, the term of this patent is extended or adjusted under 35 U.S.C. 154(b) by 280 days.

(21) Appl. No.: 11/452,725

(22) Filed: Jun. 13, 2006

(65) Prior Publication Data
US 2007/0287198 A1    Dec. 13, 2007

(51) Int. Cl.
*G01N 33/53*    (2006.01)
(52) U.S. Cl. ............... 436/514; 436/518; 436/520; 436/523; 436/531; 436/535; 436/807; 436/808; 436/810; 435/287.1; 435/287.7; 435/805; 435/810; 435/4; 435/287.8; 435/287.9; 435/288.2; 435/288.4; 435/288.5; 422/50; 422/56; 422/58; 422/60; 422/61
(58) Field of Classification Search ........... 436/514, 436/518, 520, 523, 531, 535, 807, 808, 810; 435/287.1, 287.7, 805, 810, 4, 287.8, 287.9, 435/288.2, 288.4, 288.5; 422/50, 56, 58, 422/60, 61
See application file for complete search history.

(56) References Cited
U.S. PATENT DOCUMENTS

| 3,981,776 A | 9/1976 | Saxholm |
| 4,011,942 A | 3/1977 | Crosslen |
| 4,168,146 A | 9/1979 | Grubb et al. |
| 4,305,924 A | 12/1981 | Piasio et al. |
| 4,336,241 A | 6/1982 | Diamond et al. |
| 4,632,901 A | 12/1986 | Valkirs et al. |
| 4,743,560 A | 5/1988 | Campbell et al. |
| 4,883,760 A | 11/1989 | Heelies |
| 4,943,522 A | 7/1990 | Eisinger et al. |
| 5,395,498 A | 3/1995 | Gombinsky et al. |
| 5,416,000 A | 5/1995 | Allen et al. |
| 5,445,970 A | 8/1995 | Rohr |
| 5,474,902 A | 12/1995 | Uylen et al. |
| 5,476,796 A | 12/1995 | Takahashi et al. |
| 5,591,645 A | 1/1997 | Rosenstein |
| 5,602,040 A | 2/1997 | May et al. |
| 5,622,871 A | 4/1997 | May et al. |

(Continued)

FOREIGN PATENT DOCUMENTS

| WO | 0171344 | 9/2001 |
| WO | 2004011942 | 2/2004 |

OTHER PUBLICATIONS

International Search Report and Written Opinion of the International Searching Authority, 5 pages (Jan. 25, 2008).

*Primary Examiner*—Bao-Thuy L Nguyen
(74) *Attorney, Agent, or Firm*—The Maxham Firm (57) ABSTRACT A diagnostic assay device that directs an applied sample to the analytical membrane of a directed flow device. The device has a sample receiving port defined by layers of built-up material on one end of the test strip. The port contains the sample and specifically directs it to the membrane in a controlled fashion. Additional features include configuration of the housing in a general C-shape with the test strip spanning the opening of the C-shape to allow access by a reader device. A preferred method employs superparamagnetic particles to label the target analytes for detection and measurement by means of an electromagnetic reader device.

5 Claims, 4 Drawing Sheets

U.S. PATENT DOCUMENTS

| | | |
|---|---|---|
| 5,714,389 A | 2/1998 | Charlton et al. |
| 5,723,345 A | 3/1998 | Yamauchi et al. |
| 5,728,587 A | 3/1998 | Kang et al. |
| 5,798,273 A | 8/1998 | Shuler et al. |
| 5,817,526 A | 10/1998 | Kinoshita et al. |
| 5,879,951 A | 3/1999 | Sly |
| 5,922,284 A | 7/1999 | Kinoshita et al. |
| 5,925,573 A | 7/1999 | Colin et al. |
| 5,958,790 A | 9/1999 | Cerny |
| 5,981,297 A | 11/1999 | Baselt |
| 5,998,220 A | 12/1999 | Chandler |
| 6,017,767 A | 1/2000 | Chandler |
| 6,136,549 A | 10/2000 | Feistel |
| 6,187,598 B1 | 2/2001 | May et al. |
| 6,248,598 B1 | 6/2001 | Bogema |
| 6,258,045 B1 | 7/2001 | Ray et al. |
| 6,352,862 B1 | 3/2002 | Davis et al. |
| 6,358,752 B1 | 3/2002 | Durst et al. |
| 6,485,982 B1 | 11/2002 | Charlton |
| 6,534,320 B2 | 3/2003 | Ching et al. |
| 6,607,922 B2 | 8/2003 | LaBorde |
| 7,046,357 B2 * | 5/2006 | Weinberger et al. ......... 356/246 |
| 2004/0214347 A1 * | 10/2004 | LaBorde et al. ............. 436/518 |

* cited by examiner

DIRECTED-FLOW ASSAY DEVICE

BACKGROUND OF THE INVENTION

1. Field of the Invention

The present invention relates generally to immunoassays, receptor-, cellular-, and molecular-based assays, and liquid delivery devices incorporating the same. More specifically it relates to an analytical assay or test device containing a liquid delivery element and may contain reagents for detection of an analyte of interest.

2. Discussion of Related Art

Various chromatographic and microfluidic immunoassay techniques have been available for some time. For example, immune-based latex agglutination tests for detecting a factor associated with rheumatoid arthritis were used as early as 1956 (Singer et al., Am. J. Med. 22:888-892 (1956)). Tests that can be performed with such chromatographic and fluid systems often involve immunoassays, which depend on the specific interaction between an antigen and a corresponding antibody. Immunoassays therefore have gained consideration as an important and convenient means of testing for the presence or the amount, or both, of clinically important molecules.

Among the many analytical systems used for detection of analytes, particularly those of biological interest, are chromatographic and fluidic assay systems. Among the analytes frequently assayed with such systems are: (1) hormones, such as human chorionic gonadotropin (hCG), which is frequently assayed as a marker of human pregnancy; (2) antigens, particularly antigens specific to bacterial, viral, and protozoan pathogens, such as streptococcus, hepatitis virus, and giardia; (3) antibodies, particularly antibodies induced as a result of infection with pathogens, such as bacteria or viruses, such as HIV; (4) other proteins, such as hemoglobin, frequently assayed in determinations of fecal occult blood, an early indicator of gastrointestinal disorders such as colon cancer; (5) enzymes, such as aspartate aminotransferase, lactate dehydrogenase, alkaline phosphatase, and glutamate dehydrogenase, frequently assayed as indicators of physiological function and tissue damage; (6) drugs, both therapeutic drugs, such as antibiotics, tranquilizers, and anticonvulsants, and illegal drugs of abuse, such as cocaine, heroin, and marijuana; (7) vitamins; and (8) nucleic acid material.

Such chromatographic systems are frequently used by physicians and medical technicians for rapid in-office diagnosis. They are therefore commonly referred to as "point of care" (POC) devices. These tests may also be used for therapeutic monitoring of a variety of conditions and disorders. They are also increasingly used by: patients themselves for at-home monitoring of such conditions and disorders; scientists for use in field testing for transgenic crops and environmental contaminates; soldiers in battlefield conditions for biological warfare weapon detection; and veterinary and emergency technicians where rapid testing is crucial.

The chromatographic and fluidic techniques used in conjunction with most common immunoassays involve the principle of immunochromatography. In general, this technique uses a label or indicator particle that has been linked to an immunoprotein specific for the molecule to be assayed. The label and antibody/antigen together are referred to as a conjugate, which is then mixed with a specimen. If the analyte molecule is present in the specimen, the conjugate specifically binds to the molecule. The label aspect provides a detectable indication that the molecule to be assayed is present. The specific reactions that are employed vary with the nature of the molecule being assayed and the sample to be tested. Such determinations are readily made depending on the molecule of interest.

Immunochromatographic and fluidic assays fall into two principal categories: "sandwich" and "competitive," according to the nature of the antigen-antibody complex to be detected and the sequence of reactions required to produce that complex. In the case of antigen detection, the sandwich immunochromatographic procedures call for mixing the sample that may contain the analyte to be assayed with antibodies to the analyte. These antibodies are mobile and typically are linked to a label or a reagent, such as dyed latex, a colloidal metal sol, or a radioisotope. This mixture is then applied to a chromatographic medium containing a band or capture zone. This band or capture zone contains immobilized antibodies for the analyte of interest. The chromatographic medium can also be in the form of a strip resembling a dipstick. When the complex of the molecule to be assayed and the labeled antibody reaches the zone of the immobilized antibodies on the chromatographic medium, binding occurs, and the bound-labeled antibodies are localized at the zone. This indicates the presence of the molecule to be assayed. This technique can be used to obtain qualitative results. Examples of sandwich immunoassays performed on test strips are described in U.S. Pat. Nos. 4,168,146 to Grubb et al., 4,366,241 to Tom et al., 6,017,767 and 5,998,220 to Chandler; and 4,305,924 to Piasio et al.

In competitive or indirect immunoassays, the immobilized component is typically present in controlled amounts and the mobile component is present in unknown amounts. The unknown amount of mobile component is supplemented with a known amount of the same component that has been tagged by the addition of a measurable constituent which does not interfere with its immunochemical reactive properties. The tag may consist of a radioisotope, a chromophore, a particle, a fluorophor, or an enzyme. The amount of tagged material bound immunochemically to the solid phase will depend upon the amount of untagged component in solution competing for the same binding sites. The more of the unknown component present, the less will be the amount of bound tagged component. As such a relative determination can be made.

Enzyme-based chromatographic assays have gained use in addition to immunochromatographic assays. These enzyme-based assays involve an enzymatically-catalyzed reaction instead of an antigen-antibody reaction. The enzymatically-catalyzed reaction frequently generates a detectable product.

Although useful, currently available chromatographic techniques using test strips have a number of drawbacks. Some samples, for example, fecal samples, contain particulate matter that can obscure or color the pores of the chromatographic medium, greatly hindering detection of the labeling reagents. Blood for example, obviously contain cells and colored components that obscure the color generation in the test, and therefore make it difficult, if not impossible, to read. Blood cells also tend to clog the pores in the medium. Wet chromatographic medium is also sometimes difficult to read because of specular reflection from the chromatography medium. There are various other drawbacks to chromatographic techniques, including physical properties of lateral flow, fluid front movement along the strip, and color generation intensity and location.

Sample preparation and waste generation are responsible for other problems with currently available devices and techniques for fluidics and immunochromatography. The increased prevalence of diseases spread by infected blood and blood fractions, such as HIV and hepatitis, has only exacerbated these concerns. The available forms of lateral flow devices have a large portion of their components that are only used for mechanical support of the chromatographic membrane, and are not sealed. Therefore disposal is a concern, expensive, and possibly hazardous because of the presumed bio-hazards. Precautions have to be taken so that workers, or people who may inadvertently come into contact with the waste, do not themselves become contaminated.

One common aspect of known devices, particularly in lateral flow technology and microfluidic systems, is that the assay is read visually, that is, by means of one or more optically readable lines on a test strip held in a carrier or through "windows" in the device, which may have various configurations. As briefly indicated above, there are several limitations or disadvantages to the known optically detected assays. Because they are optical, only surface changes (typically coloration) can be detected. In addition, these tests are only appropriate where the sample solution is colorless. Also, the target analytes may be in the sample solution but of such a low concentration that only relatively few are captured in the capture zone of the assay. This may provide a faint or even non-optically detectable reading, and a false negative reading can result. Quantitative assessments are only an estimation based on color intensity of the detection line. Because the prior art assays are optically read, they are subject to contamination by exposure and light-caused degradation. Therefore, they have a limited archival shelf life.

Typically one end of the test is exposed to the sample, normally a fluid of some type, being tested for the particular target analytes of interest. The fluid migrates through a capillary or chromatographic medium whereby the analyte with its label is captured and immobilized, while the remaining fluid is absorbed into a medium at the distal end of the assay. Examples of optically read lateral flow devices and methods are shown in U.S. Pat. Nos. 5,591,645; 5,798,273; 5,622,871; 5,602,040; 5,714,389; 5,879,951; 4,632,901; and 5,958,790.

Many current devices also have a liquid sample application member in direct fluid communication with the test strip. Typically this member is made from an absorbent material that may be contained within the device itself, or may protrude from the device to be more easily introduced to the liquid sample. The absorbent liquid sample application member attempts to control the rate of flow of fluid through the device. The concern is that if the liquid sample is applied directly to the test strip, the strip may be easily flooded and the assay rendered ineffective. Also the application member is usually made from a different material than the test strip itself due to the relatively large quantity of liquid that it is expected to manage.

Others have attempted to control the rate of fluid flow to the test strip by employing capillary assay formats. Examples of capillary assays can be found in U.S. Pat. Nos. 4,883,760 and 5,474,902. However, these are not an appropriate scale for use in point-of-care situations.

Biological systems other than lateral flow immunoassays have employed magnetic particles or microbeads, which may be more specifically referred to as superparamagnetic iron oxide impregnated polymer beads. These beads bind with the target analytes in the sample being tested and are then typically isolated or separated out magnetically. Once isolation has occurred, further testing may be conducted, including observing particular images, whether directly optically or by means of a camera. Examples of these systems may be found in U.S. Pat. Nos. 3,981,776; 5,395,498; 5,476,796; 5,817,526; and 5,922,284.

Another apparatus for detecting target molecules in a liquid phase is shown in U.S. Pat. No. 5,981,297 where magnetizable particles are employed and the output of magnetic field sensors indicates the presence and concentration of target molecules in the sample being tested. Other examples to sense magnetically using physical forces are disclosed in U.S. Pat. Nos. 5,445,970; 5,981,297; and 5,925,573. However, in these devices, the magnet requires relatively high power because the gap where the assay is placed must be wide enough to accommodate the relatively thick assay device.

Accordingly, it would be advantageous to have a testing device where the fluid sample is applied in such a manner that avoids the problems of prior art devices, that has a detection region providing standardized, reliable, and reproducible results, and that is also archival for storage over time. The present invention satisfies these needs and provides related advantages as well.

SUMMARY OF THE INVENTION

The present invention relates generally to immunoassays, cellular- and molecular-based assays. More specifically, it relates to directed flow assays that have a sample receiving port separated by a micro-channel from the analytical membrane. In preferred embodiments, these assays use superparamagnetic particles as the labels for the analytes to be detected. The bound complexes of labeled particles and analytes are captured in predetermined areas or regions on the test strip and the presence and quantity of labeled analytes are then detectable by magnetic means. It is also contemplated in some embodiments that the analytes may be detected by routine optical means, for example. Specific reagents and conjugates necessary for optical detection have been in use for many years and are well known.

In one embodiment, the device has an assay support member having a first end and a second end and a porous analytical membrane mounted adjacent to and generally parallel with the support member. The analytical membrane has a first end and a second end, and at least one capture region intermediate the first and second ends where at least one capture region is configured to capture labeled analytes moving from the first end of the analytical membrane toward the second end of the analytical membrane.

The devices herein also preferably have a sample receiving port, preferably connected via a channel, or in fluid communication with, the test strip itself. In these embodiments, a sample application member, or sample pad, is not strictly necessary. The sample receiving port has an appropriate size and construction to hold a desired amount of fluid and is in direct fluid communication with the test strip. The sample receiving port is at one end of the support member for introduction of the sample to be analyzed to said device. The sample receiving port has a fluid sealing material, and a channel layer positioned adjacent the sealing material. The channel layer has an opening therein and also a channel, such that the opening provides fluid communication with the channel, and such that the channel provides fluid communication with the porous analytical membrane. A hydrophilic material is positioned over the channel layer and has an opening therein corresponding to the opening of the channel layer. A gasket element is positioned over the hydrophilic material and has an opening therein to allow fluid entry into the port. The gasket provides a seal between the assay and any surrounding housing.

Additional embodiments of the invention may have a protective membrane covering the analytical membrane on the side opposite to the support member. The protective membrane may be optically non-transparent. In other embodiments the protective membrane is formed integrally with the porous membrane. Alternatively, the protective membrane may be formed pursuant to a surface treatment of the porous membrane.

Additional embodiments of the invention may have a control region in the porous membrane for collection of magnetic conjugates that have passed the capture region to show that the test strip has been used. In additional embodiments at least one magnetic calibration area may be printed on the protective membrane. The calibration area may have the form of a line, or even a single dot, among others.

Preferred embodiments of the invention have a bottom housing portion for supporting the support member. This housing will preferably be in a C-shape, although many other shapes are contemplated herein as long as access by a reader device to the test strip is provided. A top housing portion may also be present in these embodiments. This top housing portion preferably has a complementary configuration to the bottom housing portion and fits over the bottom housing portion such that the immunoassay test strip spans the opening of, or the arms of, the C-shape.

The invention further provides various methods employing the devices described herein. For example, a method is provided for conducting lateral flow immunoassay quantitative detection of target analytes in a sample. The method involves coupling superparamagnetic conjugate particles configured to bind with a desired target analyte in the sample. The analyte and superparamagnetic particle complex is applied to one end of the assay and delivered to the porous membrane of a lateral flow test strip through a sample receiving port. The complexes of analyte and superparamagnetic particles move through the porous membrane by capillary action. Next, the quantity of labeled analytes in the capture region is read by means of a magnetic assay reader device.

The present invention has improved sensitivity over known lateral flow devices. It provides a very rapid (within a few minutes) analytical measurement. There are many advantages of using magnetic particles over known colored particles or other optical indicators in the prior art. These include quantitative linearity of magnetic detection with respect to the amount of magnetic material present over a wide range, through at least four orders of magnitude. Time stability is also superior because magnetic particles are stable, thereby allowing the developed assay to be archived and retested as necessary. Further, magnetic particles are generally inert to biological systems and to the environment. So they not only remain stable, they are environmentally and biologically safe. Further, magnetic particles are already in widespread use with other technologies throughout the diagnostics industry so they are readily available. Other benefits of magnetic detection are that since the particles are superparamagnetic, they are magnetic only when exposed to a magnetic field. This allows them to be freely manipulated in solution without aggregating.

Another significant advantage over the prior art optical lateral flow devices is that with this invention the total amount of analytes in the capture region of the test strip is measured as a single mass in one volumetric measurement. The permeability of magnetic fields is such that any analyte contained within the active region of the detector will be measured. This contrasts with optical sensing techniques in which only reporter-analyte interactions on or very near the surface of the strip are detectable. In this invention the strength of the magnetic signal increases directly with the mass of iron involved, unrelated to its proximity to the surface of the strip. This inherent linearity of magnetic detection contributes to increased sensitivity, accuracy, and dynamic range. Additionally, superparamagnetic particles are physically similar to colloidal gold with regard to size, and may be easily adapted to a wide range of lateral flow assays. It is noted that colloidal gold, as well as fluorescent latex particles, are typically employed in the prior art optically sensed immunological assays.

In most lateral flow devices, typically at one end of the porous membrane is the sample introduction area. This is conventionally made up of a sample pad and a conjugate pad. In the prior art, the conjugate pad is the source of freely moveable colored particles, typically gold sols from colloidal gold, or fluorescent latex particles. In various embodiments of the present invention, there is no sample pad or conjugate pad. The moveable particles are the superparamagnetic particles which label the target analytes from the sample being introduced through the fluid channel. In preferred embodiments herein, the sample is mixed with the superparamagnetic particles before the sample is applied to the device, or at the same time. Various functional advantages exist with this configuration. For example, the reaction kinetics of particles in solution assures that the reaction is faster, provides more complete incubation, and runs to completion. By contrast, when the reaction proceeds in a wave front on a porous membrane, the reaction tends to be slower and the possibility exists that it will not reach an end point as fast, or at all.

The sample, together with the bound magnetic particle labels and target analytes, move with capillary action along the porous membrane and are captured in a predefined location called a capture region or capture zone. There may be more than one capture zone to enable multiplexing. As used herein, the term "multiplexing" refers to testing for more than one type of analyte at the same time in the same test strip. Excess analytes and the carrying liquid continue to move on through the capture zone to the other end of the porous membrane, sometimes forming a control line or zone separate from the capture zone. An added feature is that typically a wicking pad is mounted on the far end of the porous membrane to enhance the capillary action by driving the flow from the introduction at one end of the porous membrane through the entire length of the membrane.

In the embodiments herein not using optical detection, the top of the porous member may be covered by another protective sheet or membrane which is not transparent. It may be completely opaque. This top sheet may also include preprinted standards, which are employed for calibrating purposes so that the magnetic detector can be calibrated for each test to ensure complete accuracy. The protective sheet may not be a separate element in some cases, but may only be the upper surface of the membrane properly treated to function as a protective sheet or surface.

BRIEF DESCRIPTION OF THE DRAWING

These and other aspects, features and advantages of the present invention will become more apparent upon consideration of the following description of preferred embodiments taken in conjunction with the accompanying drawing, in which like reference numerals designate like parts throughout.

DETAILED DESCRIPTION OF THE PREFERRED EMBODIMENTS

In the following description of preferred embodiments, reference is made to the accompanying drawings, which form a part hereof, and which show by way of illustration, specific embodiments of the invention. It is to be understood by those of working skill in this technological field that other embodiments may be utilized, and structural, as well as procedural changes may be made without departing from the scope of the present invention.

With reference now to FIGS. 1 to 5, directed flow assay device 10 in accordance with the present invention comprises immunoassay test strip 12, which has porous analytical membrane 14 mounted adjacent to and generally parallel with support member 11. Adhesive layer 13 (FIG. 2) anchors analytical membrane 14 to support member 11. The analytical membrane has a first end and a second end.

Figure 1:
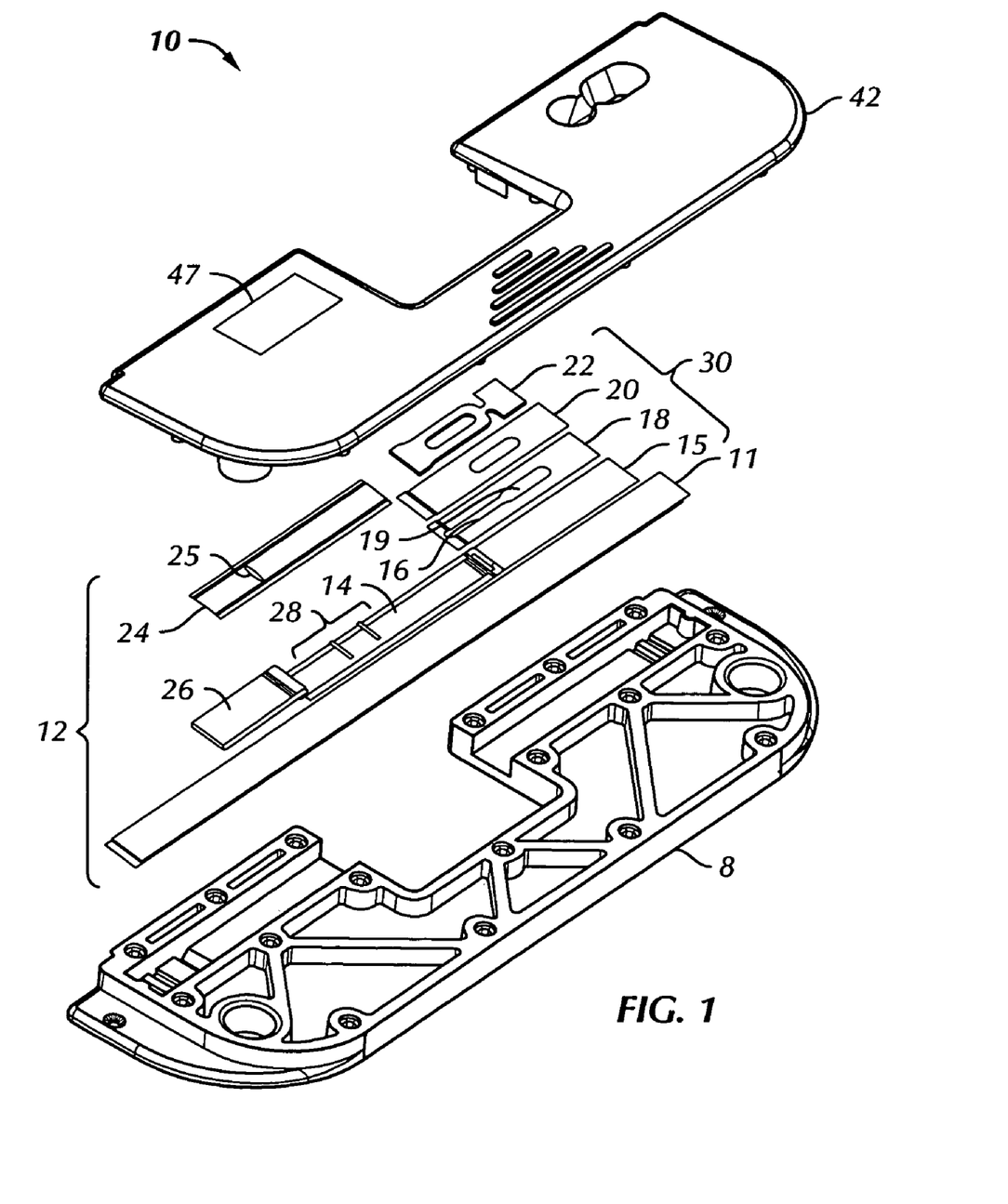
FIG. 1 is an exploded perspective view of a directed flow assay device in accordance with the present invention.
Figure 2:
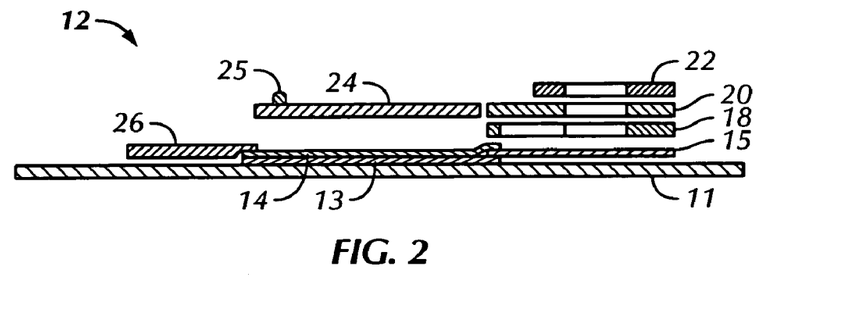
FIG. 2 is a side sectional view of the assembled test strip of FIG. 1.

Superparamagnetic particles (not shown) may be present in the sample preparation outside the device. These particles are configured to bind with the target analytes in the sample. The membrane has a capture region intermediate to the first and second ends of the analytical membrane. The capture region generally has control and detection regions 28, shown in FIG. 1. The capture region is configured to capture labeled analytes moving from the first end of the analytical membrane toward the second end of the analytical membrane. Additional regions may be present, if desired, for example, for calibration. See, for example, calibration strips 25 (FIGS. 1 and 2) on protective membrane 24. This could equally be a dot, such as dot 27 in FIG. 5. As shown in FIG. 2, it could be either a line or a dot.

One aspect of the present invention is that it has sample receiving port 30 at one end of strip 12 for introduction of the sample to be analyzed. In prior devices, the sample receiving port is generally formed by the housing of the device, if at all. In the present invention, the sample receiving port is located generally on the strip, and is made or built up from layers of applied material.

The sample receiving port is formed by fluid sealing material 15 on the bottom, which is positioned over the support member. Preferably fluid sealing material 15 is hydrophilic. Layer 18 is positioned over the fluid sealing material and has channel 16 and opening 19 formed therein. Channel 16 extends longitudinally along the strip to direct fluid toward the capture region of the device. Generally the channel is constructed of sufficient dimension and configuration to allow sufficient fluid flow without fluid leakage out of the sides or without exhibiting clogging or clumping, as might otherwise occur with more viscous samples, such as blood. Although FIG. 1 shows channel 16 being somewhat narrower than opening 19, it is contemplated herein that channel 16 could be the same width or even wider than opening 19. Alternatively, channel 16 could have a wider opening distal to the sample receiving port than its width proximal to the sample receiving port. This variation could be particularly useful in the case where clotting or clumping of the sample is of concern.

Once built up in layers, the sample receiving port is formed. The port provides fluid communication with the channel, and the channel provides fluid communication with the analytical membrane. Next hydrophilic material 20 is positioned over layer 18, the hydrophilic material having an opening therein corresponding to opening 19, but covering channel 16. Gasket element 22 is positioned over hydrophilic material 20 and has an opening therein corresponding to opening 19 to allow fluid entry into the port. The gasket provides a fluid seal between the assay and any surrounding housing.

Figure 3:
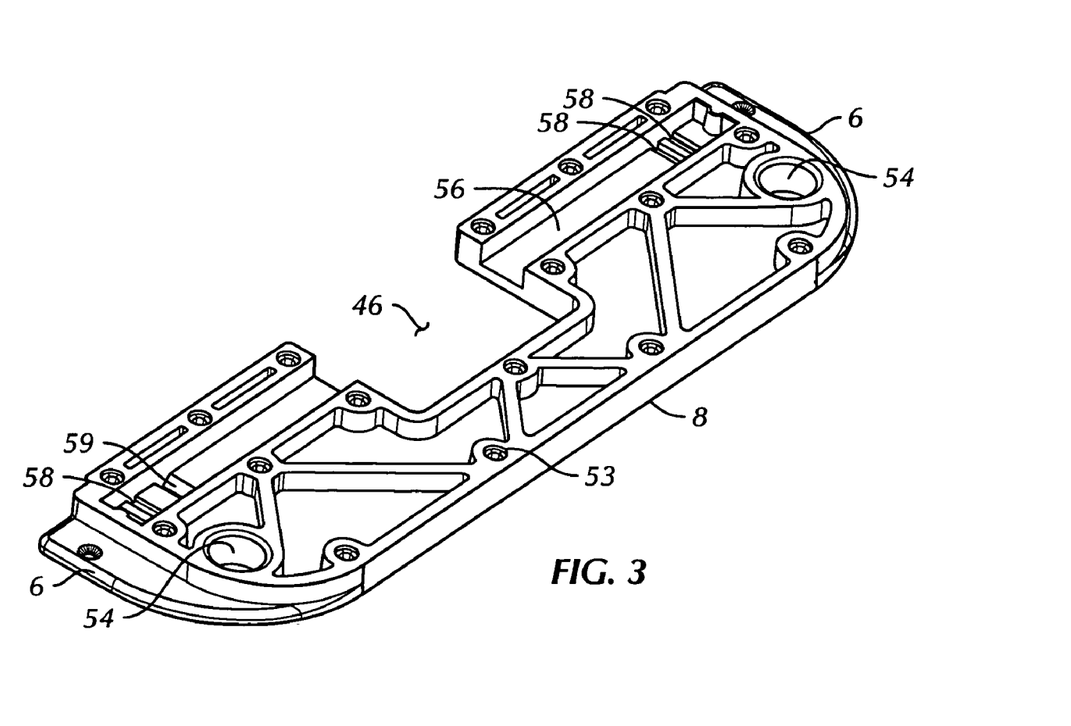
FIG. 3 is a perspective view of the bottom housing portion of the device of FIG. 1.
Figure 4:
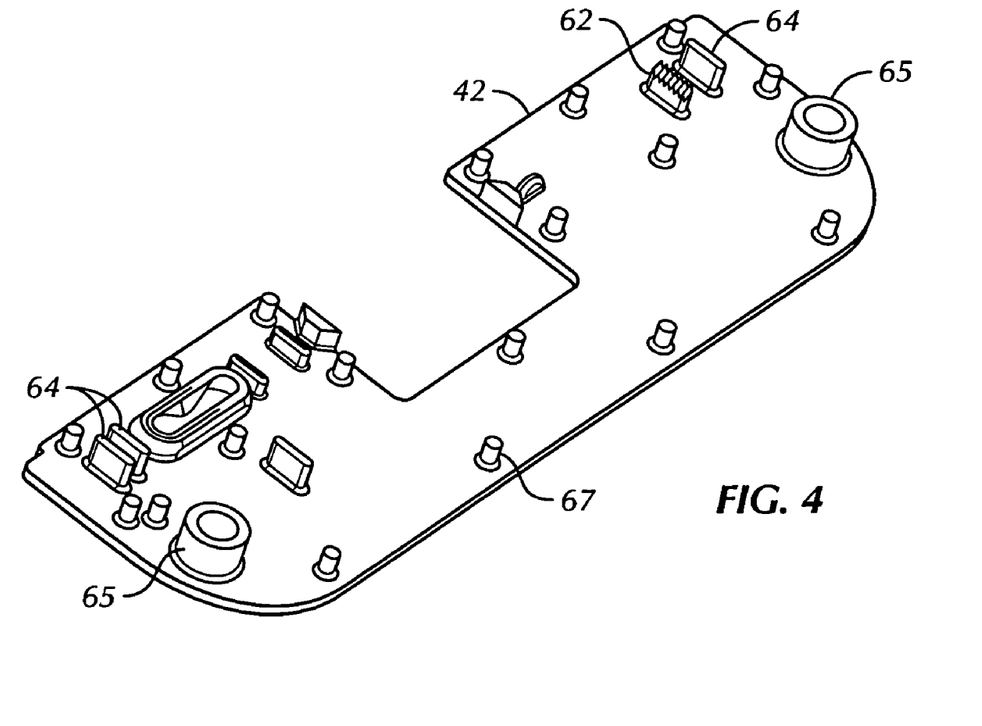
FIG. 4 is a perspective view of the inside of the top housing portion of the device of FIG. 1.
Figure 5:
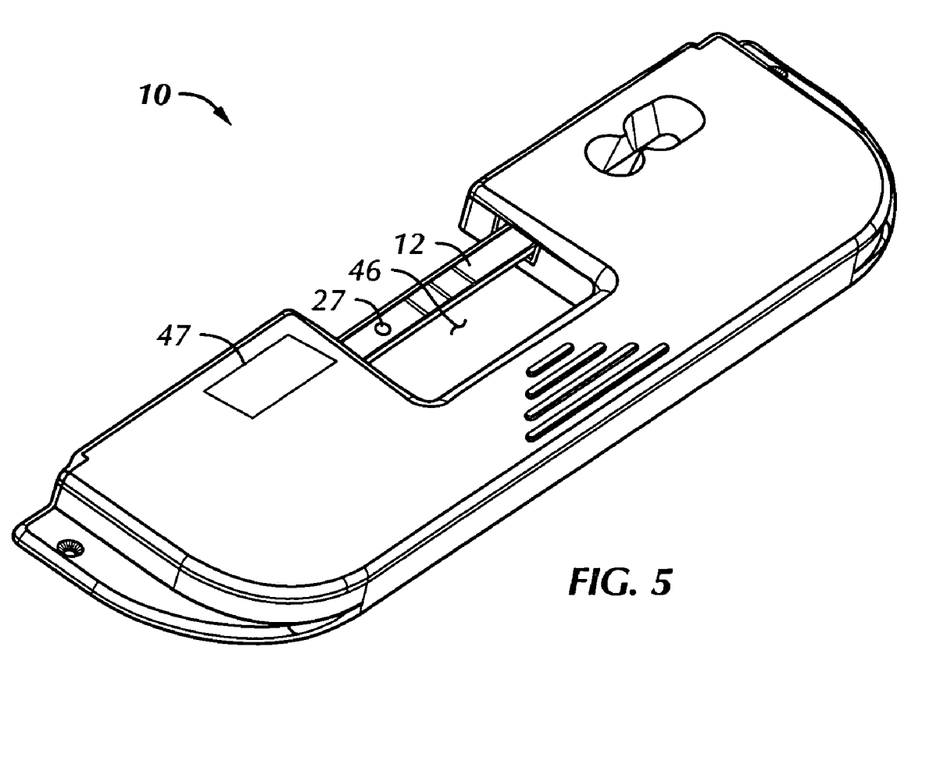
FIG. 5 is a perspective view of the fully assembled device of the present invention.

In various embodiments described herein, the housing is made up of bottom housing portion 8 which supports support member 11. As shown in FIG. 3 it also preferably has side tabs 6 for proper placement in a magnetic reader device. Bottom housing portion 8 is generally configured in a C-shape, the open side being designated by reference numeral 46. FIG. 4 shows the underside of top housing portion 42. It is generally complementary in configuration to the bottom housing portion. Therefore, it is also in a C-shape configuration. The top housing fits over the bottom housing such that test strip 12 spans opening 46 of the C-shape, as shown in the assembled device of FIG. 5. Thus, a magnetic reader device can access test strip 12 from the top and bottom surface at the same time. FIG. 2 shows a sectional side view of assembled test strip 12. Wicking pad 26 is present on one end, as well as protective membrane 24, which covers analytical membrane 14.

Since test strip 12 spans opening 46 of the assembled housing portions, and since it is placed in the gap of a magnetic reader device, it is of concern that the test strip be properly anchored within the housing so as to avoid flexing or movement of the strip with relation to the housing portions. It is also important that the relative positions of the control line, index line, and result lines be maintained. Accordingly, the embodiments of the present invention have gripping and tensioning aspects to control these effects.

With reference again to FIG. 3, bottom housing portion 8 is shown in a perspective view. Although not shown in this view, test strip 12 is dropped into trough 56. Preferably the width of the trough will accommodate the width of the strip without binding or without undesired lateral movement. Cross channels 58 are present in the bottom of trough 56. There are preferably two such cross channels closely spaced at one end, and one cross channel at the other end of the trough. Also at one end of the trough there is sloping cross channel 59. These channels are configured to accommodate corresponding features on the underside of top housing portion 42 when assembled. Accordingly, the assembly thereof provides a gripping and tensioning aspect to the test strip.

As shown in FIG. 4, the underside of top housing portion 42 has pegs 64, two on one end, and one on the other end of the device. Also on one end of the device is tensioner 62. Tensioner 62 is shown with a downward sloping face and a scalloped or ridged protruding edge. This edge contacts the test strip and provides an appropriate degree of tension without causing deformation or tearing of the strip. The configuration shown is by way of example and the tensioner may have other equally effective shapes.

Other features of the device are directed toward preventing movement of the strip in relation to the magnetic field. For example, bottom housing portion 8 has securing holes 54 for receiving securing pins 65 on top housing portion 42. The relatively large diameter of the hole and pin secures the parts together to prevent undesired warping or bending of the housing components once assembled. Also it can be seen in FIG. 3 that assembly holes 53 in the bottom housing portion are configured to receive assembly pins 67 in the top housing portion, preferably with a compression fit.

As mentioned above, FIG. 5 shows an embodiment of the device fully assembled. Test strip 12 is shown spanning opening 46. Barcode label area 47 on top housing portion 42 provides information that the magnetic reader device uses in the assay, such as calibration and positional information. It also may provide information regarding the nature of the particular test or sample being tested for.

It should be observed that while the above description generally relates to quantitative detection of target analytes in a directed flow immunoassay, the invention can equally be used for receptor assays, cellular assays, or molecular assays.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A lateral flow assay device for quantitative detection of target analytes in a sample, said device comprising:
    an assay support member having a first end and a second end;
    a porous analytical membrane mounted adjacent to and generally parallel with said support member, said analytical membrane having a first end and a second end and at least one capture region intermediate said first and second ends thereof, said at least one capture region being configured to capture labeled analytes moving from said first end of said analytical membrane toward said second end of said analytical membrane; and
    a sample receiving port at one end of said support member for introduction into said device of the sample to be analyzed, said sample receiving port comprising:
    a fluid sealing material on said support member;
    a channel layer positioned above said sealing material, said channel layer comprising an opening and a channel, said opening providing fluid comunication with said channel, and said channel providing fluid communication with said porous analytical membrane;
    a hydrophilic material positioned over said channel layer, said hydrophilic material having an opening therein corresponding to said opening in said channel layer; and
    a gasket element positioned over said hydrophilic material and having an opening therein to allow fluid entry into the port, said gasket providing a fluid seal for the assay device.

2. The device recited in claim 1, and further comprising a protective membrane covering said analytical membrane on the side opposite to said support member, said protective membrane being optically non-transparent.

3. The device recited in claim 2, wherein said protective membrane is formed integrally with said porous membrane.

4. The device recited in claim 1, and further comprising a control region in said porous membrane for collection of conjugates that have passed the capture region to show that said test strip has been used.

5. The device recited in claim 4, and further comprising at least one magnetic calibration area printed on said protective membrane.

* * * * *

UNITED STATES PATENT AND TRADEMARK OFFICE
CERTIFICATE OF CORRECTION

PATENT NO. : 7,547,557 B2
APPLICATION NO. : 11/452725
DATED : June 16, 2009
INVENTOR(S) : Ronald T. LaBorde et al.

It is certified that error appears in the above-identified patent and that said Letters Patent is hereby corrected as shown below:

In col. 9, line 22, "generatly" should read --generally--.

Signed and Sealed this
Twenty-second Day of March, 2011

David J. Kappos
*Director of the United States Patent and Trademark Office*